(12) United States Patent
Goeders et al.

(10) Patent No.: US 10,702,537 B2
(45) Date of Patent: *Jul. 7, 2020

(54) DEVICES AND METHODS OF TREATING METHAMPHETAMINE ADDICTION AND MEDICAL AND BEHAVIORAL CONSEQUENCES OF METHAMPHETAMINE USE AND OF HIV INFECTION

(71) Applicant: Board of Supervisors of Louisiana State University and Agricultural and Mechanical College, Baton Rouge, LA (US)

(72) Inventors: Nicholas E. Goeders, Shreveport, LA (US); Christopher Dalton Schmoutz, Shreveport, LA (US)

(73) Assignee: BOARD OF SUPERVISORS OF LOUISIANA STATE UNIVERSITY and Agricultural and Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/997,020

(22) Filed: Jun. 4, 2018

(65) Prior Publication Data

US 2019/0224211 A1 Jul. 25, 2019

Related U.S. Application Data

(62) Division of application No. 15/175,284, filed on Jun. 7, 2016, now Pat. No. 10,022,383.

(60) Provisional application No. 62/190,287, filed on Jul. 9, 2015, provisional application No. 62/182,054, filed on Jun. 19, 2015.

(51) Int. Cl.
*A61K 31/5513* (2006.01)
*A61K 31/5517* (2006.01)
*A61K 31/501* (2006.01)
*A61K 31/603* (2006.01)
*A61K 31/568* (2006.01)
*A61K 45/06* (2006.01)

(52) U.S. Cl.
CPC ........ *A61K 31/5513* (2013.01); *A61K 31/501* (2013.01); *A61K 31/5517* (2013.01); *A61K 31/568* (2013.01); *A61K 31/603* (2013.01); *A61K 45/06* (2013.01)

(58) Field of Classification Search
CPC .................................................. A61K 31/55113
See application file for complete search history.

(56) References Cited

U.S. PATENT DOCUMENTS 5,776,946 A * 7/1998 McGeer ............... A61K 31/472
514/221

OTHER PUBLICATIONS

Zhang et al. Neuroscience, 2008, vol. 152, pp. 502-510.*
Strauss J.F. The Synthesis and Metabolism of Steroid Hormones, Yen & Jaffe's Reproductive Endocrinology (Sixth Edition), 2009, pp. 1-12.*
Wolff et al. Annals of the Rheumatic Diseases, First published May 2014, vol. 74, pp. 1890-1897 and Abstract only submitted.*
Kahle et al. JAMA Neurol., 2014, vol. 71, No. 5, pp. 640-645.*

* cited by examiner

*Primary Examiner* — Samira J Jean-Louis
(74) *Attorney, Agent, or Firm* — Davis & Bujold PLLC; Michael J. Bujold

(57) ABSTRACT

A method of treating a condition of in a human patient comprising pharmacologically activating a translocator protein of 18 kDa (TSPO), wherein the condition is one of a chronic methamphetamine addiction, a medical consequence of methamphetamine use; a behavioral consequence of methamphetamine use, an HIV associated cognitive motor disorder, an HIV-associated neurodegenerative disorder, and a neuroinflammatory response.

12 Claims, 7 Drawing Sheets oxazepam alprazolam diazepam

Ro5-4864

| Pos | TSPO | GABA |
|-----|------|------|
| 1 | CH3 >> H | H = CH3 |
| 7 | Cl > F >> NO2 | Cl = NO2 > F |
| 4' | Cl > F > OCH3 >> NO2 | H > OH >> Cl > F |
| 2' | Cl > F > H | Cl > F > H |
| 3 | OH > H | H > OH |

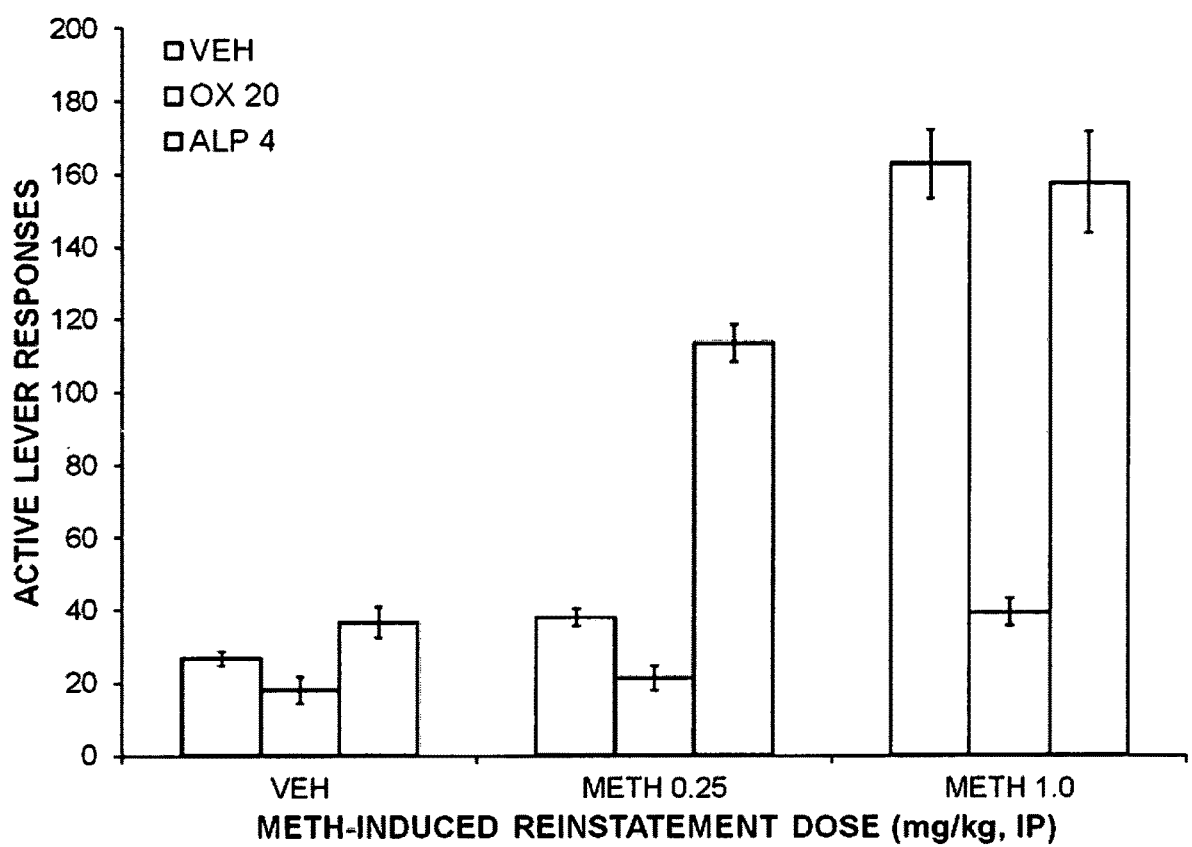

DEVICES AND METHODS OF TREATING METHAMPHETAMINE ADDICTION AND MEDICAL AND BEHAVIORAL CONSEQUENCES OF METHAMPHETAMINE USE AND OF HIV INFECTION

CROSS REFERENCE TO RELATED APPLICATIONS/PRIORITY

The present invention claims priority to U.S. Provisional Patent Application No. 62/182,054 filed Jun. 19, 2015, U.S. Provisional Patent Application No. 62/190,287 filed Jul. 9, 2015, and U.S. patent application Ser. No. 15/175,284 filed Jun. 7, 2016, which are all incorporated by reference into the present disclosure as if fully restated herein. To the extent that there is any conflict between the incorporated material and the present disclosure, the present disclosure will control.

FIELD OF THE INVENTION

The present invention relates to a methods and devices for treating methamphetamine addiction and medical and behavioral consequences of methamphetamine use and HIV infection.

BACKGROUND OF THE INVENTION

Methamphetamine abuse and related problems: Methamphetamine (MA) is a highly addictive psychomotor stimulant that is a unique drug of abuse for several reasons, not the least of which includes its user population. There has been a dramatic increase in methamphetamine use in the United States over the past 25 years, especially among women. A recent survey by the Substance Abuse and Mental Health Services Administration showed that males are more likely to use marijuana, cocaine and hallucinogens, while men and women use methamphetamine at equal rates. In addition women tend to initiate methamphetamine use earlier than men and prefer to use methamphetamine over other addictive drugs. The use of methamphetamine has been linked to cognitive defect, violence, risk-taking behaviors and criminal activity, even among female users. For example, women methamphetamine users are considered to be significantly more violent than men. While high on methamphetamine, both male and female methamphetamine users also report engaging in risky sexual behaviors (e.g., unprotected, with strangers, with multiple partners at once), decreased sexual inhibition, heightened sexual desire and arousal, and enhanced sexual pleasure, and they engage in prolonged sexual contact. These risky sexual behaviors contribute to the spread of HIV/AIDS, which has been a major public health concern for several decades.

Another particularly unique characteristic of methamphetamine use is the way in which the drug is self-administered by humans, which is typically in a "binge and crash" manner. While a clear definition of the binge use of methamphetamine is lacking in current scientific literature, according to self-reports by methamphetamine users, a binge can be described as taking methamphetamine for a long period of time "until you run out [of the drug] or just can't physically do it anymore". A methamphetamine binge in humans can range from 3-22 days. Furthermore, it has been reported that a history of unrestricted access to methamphetamine leads to increases in methamphetamine taking in both humans and animals.

Cognitive deficits (memory problems, decreased cognitive flexibility)—Data from both humans and animals show that chronic methamphetamine use can lead to disruptions of brain functioning that can affect both behavioral and neurochemical functioning, including deleterious effects on memory and cognition. Additionally, chronic methamphetamine use has been established as a risk factor for neuropsychological impairment. Approximately 40% of individuals who chronically use methamphetamine exhibit neurocognitive impairments, resulting in problems with executive functioning and psychomotor skill functioning. Even more striking, more than two-thirds of methamphetamine-dependent users exhibit impairment in overall learning, free recall and repetitions. Of particular importance are the effects of methamphetamine on episodic memory. Episodic memory is unique since it is the memory of learning a particular event, as well as what was learned during the event. Nearly 50% of methamphetamine-dependent individuals demonstrate impaired episodic memory, making it the most common type of memory affected in methamphetamine users. This impairment in episodic memory is characterized by a limited use of higher-level encoding, decreases in cognitive flexibility and increases in perseverance. Brain regions involved in cognitive function and memory include the prefrontal cortex, hippocampus, striatum and amygdala. Although the precise mechanisms by which methamphetamine disrupts episodic memory are unknown, it is generally believed that these cognitive disruptions are due to the neurotoxic effects of methamphetamine on dopaminergic, serotonergic and noradrenergic neurons in these brain regions. For example, human and animal studies have shown that depletion of dopamine (DA) in the striatum can lead to deficits in overall reaction task performance. Additionally, disruptions in serotonin (5-HT) and dopamine signaling have been shown to increase impulsivity, while depletion of central serotonin can disrupt the ability to accurately detect and respond to visual stimuli, all of which impair the ability of a subject to complete a learning or memory task.

Aberrant sexual behavior (sexual deviance, risky sexual behavior, HIV transmission)—With continued use of methamphetamine, especially when the user progresses to intravenous administration, the drug becomes primarily associated with sexual activity. The association between methamphetamine use and sexual risk taking has been well documented in men and predominantly among men who have sex with men. Studies have shown that methamphetamine use in men has been associated with high-risk sexual behaviors such as having a higher number of sexual partners, infrequent condom use, trading drugs or money for sex, having sex with a partner who is an injection drug user, as well as reports of a recent sexually transmitted infection (STI). While fewer studies have been conducted to examine the relationship between methamphetamine use and the risk of STIs among women, there are data suggesting that the proportion of methamphetamine use by either sex is more similar than with other illicit substances. Interestingly, current literature reviews suggest higher rates of bacterial STIs reported in female as compared with male drug users. Women may be more susceptible to STIs owing to the increased likelihood of asymptomatic infection and the practice of exchanging sex for money or drugs. One study of injection drug users found that methamphetamine-injecting women were more likely to have unprotected vaginal sex and multiple sex partners compared to women who injected other substances. A recent review of sexual behaviors among heterosexual drug users indicated that women methamphetamine users were at increased risk for engaging in unsafe sexual behaviors. Other studies have documented that women experience a heightened sex drive and increased number of sexual acts under the influence of methamphetamine. Qualitative data also suggest that methamphetamine use increases sexual desire and pleasure and reduces inhibition, which can alter/increase sexual behaviors in women. Recent preclinical research in rodent models of drug-induced sexual motivation also revealed a critical role for progesterone signaling in the medial amygdala on methamphetamine-related sexual behaviors in female rats. However, despite existing evidence, there is an urgent need for further research on sexual-risk behavior among women who use methamphetamine because of their potentially high risk for STIs and HIV.

There is currently not a treatment available that reduces methamphetamine cravings and medical and behavioral consequences of methamphetamine use or the HIV associated cognitive motor disorders and HIV-associated neurodegenerative disorders.

SUMMARY OF THE INVENTION

Wherefore, it is an object of the present invention to overcome the above mentioned shortcomings and drawbacks associated with the prior art.

The neurotoxic effects of HIV-1 are primarily attributed to its ability to readily penetrate into the central nervous system (CNS) early during the course of infection. Deficiency in the functionality of dopaminergic neurons has been observed to be associated with early stage HIV-1 infection. Interestingly, long-term methamphetamine use is also associated with the loss of dopaminergic neurons and functionality. Although the introduction of highly active antiretroviral therapy (HAART) has significantly reduced the incidence of HIV-associated dementia, milder neurotoxicity, including minor cognitive motor disorders and HIV-associated neurodegenerative disorders have increased in incidence. In addition, many anti-retroviral drugs fail to penetrate the blood brain barrier, thus making it difficult to treat these patients. HIV-associated neurotoxicity is primarily thought to be mediated by the neurotoxins released from infected cells, primarily resident microglia, after migration of the infected cells through the blood brain barrier. The frontostriatal regions of the brain are highly vulnerable to this so-called "Trojan Horse" mechanism by which HIV-1 penetrates the central nervous system. Methamphetamine also targets these frontostriatal regions by increasing dopaminergic and glutamatergic neurotransmission, which leads to further neuronal damage and cell death. Multiple models for methamphetamine-mediated neurotoxicity have been proposed, including a role for cross-talk between neuroinflammation induced by methamphetamine and HIV through reactive gliosis. Interestingly, activation of the translocator protein of 18 kDa (TSPO) may mediate a functional antiviral mechanism via protein misfolding during HIV glycoprotein synthesis.

As discussed more fully below, chronic methamphetamine administration results in a neuroinflammatory response characterized by a marked increase in TSPO receptor binding and microglial activation. This neuroinflammatory response is remarkably similar to effects demonstrated in patients with HIV-associated cognitive problems. Enhanced TSPO binding is seen in ~25% of HIV-positive patients, a subset who also exhibit a cluster of cognitive and executive deficits known as HIV-associated dementia. This increased TSPO binding in cortical regions is correlated to other markers of microglial activation and synaptic disruption. Even HIV-infected patients on long-term antiretroviral therapy (ART; i.e., those without viral load) show focal areas of enhanced TSPO binding in the corpus callosum, cingulate gyrus and temporal and frontal cortices. This pattern is supported by nonhuman primate research, demonstrating a similar increase in TSPO binding and neuroinflammation in simian immunodeficiency virus (SIV)-related encephalitis.

Another object of the present invention is to pharmacologically activate the translocator protein of 18 kDa (TSPO) to clinically treat cognitive and behavior consequences of methamphetamine addiction, especially chronic methamphetamine addiction, and the HIV associated cognitive motor disorders and HIV-associated neurodegenerative disorders. The TSPO agonists include Ro5-4864, other peripheral benzodiazepines or derivatives, and new compounds developed as agonists for the TSPO, especially those which have relatively low or no binding affinity for the gamma-aminobutyric acid A (GABA$_A$) receptor.

A further object of the present invention is to provide pharmacological therapies to treat specific medical consequences associated with methamphetamine addiction as well as the methamphetamine dependence itself.

The present invention also relates to a method of treating chronic methamphetamine addiction in a human patient comprising the step of administering to the patient a therapeutically effective amount of a benzodiazepine with a halogen moiety in the 4' position.

The present invention also relates to a method of treating one of HIV associated cognitive motor disorders and HIV-associated neurodegenerative disorders in a human comprising the step of pharmacologically activating the translocator protein of 18 kDa (TSPO).

The present invention also relates to a method of treating neuroinflammatory response in a human comprising the step of pharmacologically activating the translocator protein of 18 kDa (TSPO).

One aspect of the present invention relates to methods of treating a condition of in a human patient comprising pharmacologically activating a translocator protein of 18 kDa (TSPO), wherein the condition is one of a chronic methamphetamine addiction, a medical consequence of methamphetamine use, a behavioral consequence of methamphetamine use, an HIV associated cognitive motor disorder, an HIV-associated neurodegenerative disorder, and a neuroinflammatory response. In an additional embodiment the medical consequence is cognitive defect. In an additional embodiment the behavioral consequence is one of increased violence, risk-taking behaviors, propensity for criminal activity, and aberrant sexual behavior. In an additional embodiment the human is a female. An additional embodiment includes the step of pharmacologically activating the translator protein of 18 kDa (TSPO) by administering a therapeutically effective amount of a benzodiazepine that preferentially targets TSPO over a GABAA receptor. An additional embodiment includes the step of pharmacologically activating the translator protein of 18 kDa (TSPO) by administering a therapeutically effective amount of a benzodiazepine that has a halogen bound to a 4' carbon in the benzodiazepine. In an additional embodiment the translator protein of 18 kDa (TSPO) is pharmacologically activated by administering a therapeutically effective amount of one or more peripheral benzodiazepine receptor ligands selected from a group consisting of: Ro5-5115, Ro5-5119, Ro5-5120, Ro5-5122, Ro5-5888, Ro5-4864, Ro5-6524, Ro5-6528, Ro5-6531, Ro5-6900, Ro5-6902, Ro5-6945, and Ro5-6993, oxazepam and therapeutically acceptable salt, solvate, clathrate, stereoisomer, enantiomer or prodrug of these compounds or mixtures thereof. An additional embodiment includes the step of administering a therapeutically effective amount of one or more of an agonist (activator) of potassium-chloride co-transporter 2 (KCC2) and an inhibitor (antagonist) of 20 alpha-hydroxysteroid dehydrogenase (20 alpha-HSD) and therapeutically acceptable salt, solvate, clathrate, stereoisomer, enantiomer or prodrug of these compounds or mixtures thereof.

A further aspect of the present invention includes therapeutic products comprising a first component being a benzodiazepine with a halogen moiety in a 4' position or a therapeutically acceptable salt, solvate, clathrate, stereoisomer, enantiomer or prodrug of thereof, and a second component being one of an agonist (activator) of potassium-chloride co-transporter 2 (KCC2) and/or an inhibitor (antagonist) of 20alpha-hydroxysteroid dehydrogenase (20 alpha-HSD) or a therapeutically acceptable salt, solvate, clathrate, stereoisomer, enantiomer or prodrug of these compound or mixtures thereof. In an additional embodiment the first component is selected from a group consisting of: Ro5-5115, Ro5-5119, Ro5-5120, Ro5-5122, Ro5-5888, Ro5-4864, Ro5-6524, Ro5-6528, Ro5-6531, Ro5-6900, Ro5-6902, Ro5-6945, and Ro5-6993, oxazepam and therapeutically acceptable salt, solvate, clathrate, stereoisomer, enantiomer or prodrug of these compounds or mixtures thereof.

In another aspect, the present invention features a methods and devices for treating methamphetamine addiction and medical and behavioral consequences of methamphetamine use and HIV infection, where the method includes the administration of a pharmaceutical composition of an effective amount of an activator of translator protein of 18 kDa (activator of TSPO), or a pharmaceutically acceptable salt, solvate, clathrate, stereoisomer, enantiomer or prodrug thereof.

In some embodiments, the activator of TSPO, or a pharmaceutically acceptable salt, solvate, or clathrate, stereoisomer, enantiomer or prodrug thereof, is administered as a pharmaceutical composition that further includes a pharmaceutically acceptable excipient.

In some embodiments, the activator of TSPO is a compound with the basic benzodiazepine structure, but with a halogen moiety (e.g., chlorine, fluorine, bromine, iodine) in the 4' position.

In some embodiments, the mammal is a human.

In other embodiments, the activator of TSPO is administered at a dose that is between. 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more therapeutic agents for the treating methamphetamine addiction and/or medical and/or behavioral consequences of methamphetamine use and/or HIV infection.

In some embodiments, the activator of TSPO, or a pharmaceutically acceptable salt, solvate, clathrate, stereoisomer, enantiomer or prodrug thereof, is administered as a pharmaceutical composition that further includes a pharmaceutically acceptable excipient.

In some embodiments, administration of the pharmaceutical composition to a human results in a peak plasma concentration of the activator of TSPO between 0.05 µM-10 µM (e.g., between 0.05 µM-5 µM).

In some embodiments, the mammal is a human, preferably a female human.

In other embodiments, the activator of TSPO is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more therapeutic agents for the treatment or prevention of neuroinflammation.

As used herein, the term "delayed release" refers to a pharmaceutical preparation, e.g., an orally administered formulation, which passes through the stomach substantially intact and dissolves in the small and/or large intestine (e.g., the colon). In some embodiments, delayed release of the active agent (e.g., one of the TSPO compounds as described herein) results from the use of an enteric coating of an oral medication (e.g., an oral dosage form). The active agent may also be referred to as the active compound, active ingredient, active material, and/or the active drug substance.

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably refer to a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" refer to pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

By "immediate release" is meant that the agent (e.g., one of the TSPO compounds), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, represents a composition containing a compound described herein (e.g., an activator of TSPO, or any pharmaceutically acceptable salt, solvate, clathrate, stereoisomer, enantiomer or prodrug thereof), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, means a compound of the invention wherein: molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, refers to prophylactic treatment or treatment that prevents one or more symptoms or conditions of a disease, disorder, or conditions described herein (e.g., chronic methamphetamine addiction, a medical consequence of methamphetamine use, a behavioral consequence of methamphetamine use, an HIV associated cognitive motor disorder, an HIV-associated neurodegenerative disorder, and neuroinflammation). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, represents compounds which are rapidly transformed in vivo to the parent compound of the above formula. Prodrugs also encompass bioequivalent compounds that, when administered to a human, lead to the in vivo formation of an activator of TSPO.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e.

not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, impeding or reversing the progress of, or alleviating either the disease or condition to which the term applies, or one or more symptoms of such disease or condition.

The term "unit dosage forms" refers to physically discrete units suitable as unitary dosages for human subjects and other mammals, each unit containing a predetermined quantity of active material calculated to produce the desired therapeutic effect, in association with any suitable pharmaceutical excipient or excipients.

The present compounds can be prepared from readily available starting materials using the methods and procedures known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Pharmaceutical Compositions The methods described herein can also include the administrations of pharmaceutically acceptable compositions that include an activator of TSPO, or a pharmaceutically acceptable salt, solvate, clathrate, stereoisomer, enantiomer or prodrug thereof. Pharmaceutical compositions and dosage forms of the invention comprise one or more active ingredients in relative amounts and formulated so that a given pharmaceutical composition or dosage form treats methamphetamine addiction and/or medical and/or behavioral consequences of methamphetamine use and/or HIV infection. Preferred pharmaceutical compositions and dosage forms comprise a TSPO compound or a pharmaceutically acceptable prodrug, salt, solvate, stereoisomer, enantiomer, or clathrate thereof, optionally in combination with one or more additional active agents. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention (e.g. the TSPO compounds) can be administered alone, combined, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippencott Williams & Wilkins (2005), a well-known reference text in this field, and in the USP/NF (United States Pharmacopeia and the National Formulary). In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration. The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings: The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Parenteral Administration: Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery: Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences*, 81(1): 1-10, 1992)

Oral transmucosal absorption is generally rapid because of the rich vascular supply to the mucosa and allows for a rapid rise in blood concentrations of the therapeutic ("American Academy of Pediatrics: Alternative Routes of Drug Administration—Advantages and Disadvantages (Subject Review)," *Pediatrics*, 100(1): 143-152, 1997).

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art.

Formulations for sublingual administration can also be used, including powders and aerosol formulations. Exemplary formulations include rapidly disintegrating tablets and liquid-filled soft gelatin capsules.

Dosing Regimens: The present methods for treating methamphetamine addiction and medical and behavioral consequences of methamphetamine use and HIV infection, including neuroinflammation, are carried out by administering one or more TSPO compounds for a time and in an amount sufficient to result in stabilization and/or reversal of the symptoms of methamphetamine addiction and medical and behavioral consequences of methamphetamine use and HIV infection, including neuroinflammation.

The amount and frequency of administration of the compositions can vary depending on, for example, what is being administered, the state of the patient, and the manner of administration. The dosage is likely to depend on such variables as the type and extent of progression of the methamphetamine addiction, HIV infection, or neuroinflammation, the severity of the medical and behavioral consequences of methamphetamine use and HIV infection, or neuroinflammation, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of chronic tissue ischemia or slowing its progression.

The amount of TSPO compound per dose can vary. For example, a subject can receive from about 0.1 µg/kg to about 10,000 µg/kg. Generally, the TSPO compound is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of TSPO compound (e.g., 0.089-3.9 mmol) or 0.1-50 µmol of TSPO compound (e.g., 0.1-25 µmol or 0.4-20 µmol).

The frequency of treatment may also vary. The subject can be treated one or more times per day with a TSPO compound (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

KITS: Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce incidence, duration, and or severity of methamphetamine addiction, medical and behavioral consequences of methamphetamine use and HIV infection, or neuroinflammation.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 4 is bar graph showing the effects of oxazepam and alprazolam on methamphetamine induced reinstatement, where alprazolam enhanced low dose methamphetamine-induced reinstatement and oxazepam decreased methamphetamine-induced reinstatement at all doses tested;

DETAILED DESCRIPTION OF THE PREFERRED EMBODIMENTS

Figure 1A:
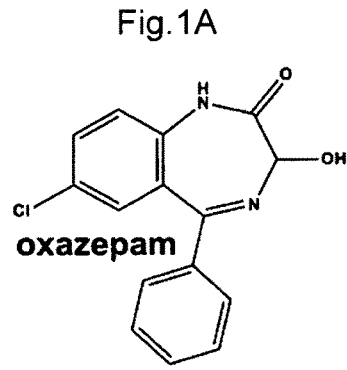
FIGS. 1A-1E are diagrams of four benzodiazepine ligands (FIGS. 1A-1D), and a diagram and table of structure-activity relationships for elements/compounds in the 1,2', 3, 4' and 7 positions on the ligands (FIG. 1E)
Figure 1B:
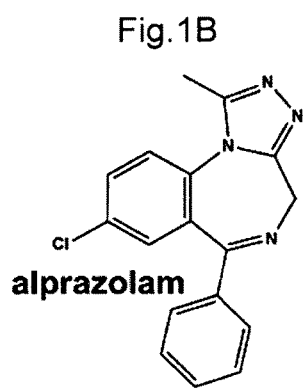
Figure 1C:
Figure 1D:
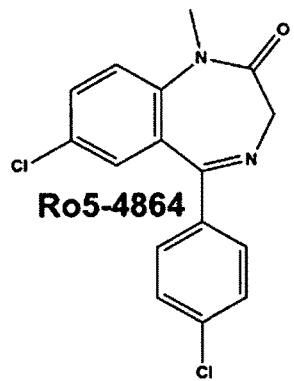
Figure 1E:
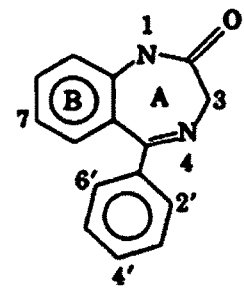

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-5, a brief description concerning the various components of the present invention will now be briefly discussed.

Benzodiazepines and psychostimulant abuse: Benzodiazepines (BZDs) can bind to two distinct binding sites:

GABA$_A$ receptors and the TSPO—Oxazepam and other benzodiazepines can increase inhibitory conductance and decrease neuronal excitability by binding to the GABA$_A$ receptor at the benzodiazepine positive allosteric modulatory site. By increasing the affinity of GABA for the receptor, benzodiazepine agonists increase the frequency of channel opening and facilitate the influx of chloride ions, resulting in a hyperpolarization of the membrane and decreased action potential propagation. This classical mechanism of action applies to nearly all benzodiazepines, including alprazolam and oxazepam. However, some benzodiazepines also have a high affinity for a second binding site, formerly known as the peripheral benzodiazepine receptor. As described above, this protein is now known as the TSPO and has a distinct pharmacology and subcellular localization when contrasted with the GABA$_A$ receptor. Importantly, many benzodiazepines, most notably diazepam and midazolam, bind to and activate the TSPO to increase neurosteroid biosynthesis. The TSPO is responsible for catalyzing the first steps of steroidogenesis by translocating cholesterol from the cytoplasm into the mitochondrial matrix. This allows cholesterol side-chain cleavage enzyme (CYP11A1; also known as P450scc) to convert cholesterol to pregnenolone, the first enzymatic conversion in the steroid biosynthesis cascade. As shown in FIG. 1, structure-activity relationships evidence that oxazepam binds to both GABA$_A$ receptors and the TSPO.

Structurally, oxazepam is nearly identical to diazepam, a prototypical agonist of both GABA$_A$ receptors and the TSPO, suggesting that oxazepam may increase neurosteroid levels by activating the TSPO. This is in contrast to alprazolam, a benzodiazepine that binds selectively to the GABA$_A$ receptor and exhibits low affinity for the TSPO. Subsequent ex vivo homogenate binding assays have confirmed the inventors' hypothesis in rat brain tissue.

Benzodiazepines affect cocaine and methamphetamine-related behaviors differently—The inventors' laboratory has long been interested in the role for benzodiazepines in drug addiction. Early research demonstrated that chronic cocaine exposure differentially affects the density of benzodiazepine receptors across several brain regions, an effect that is dependent on intact dopaminergic signaling. Additional research showed that several benzodiazepine receptor agonists could decrease cocaine related behaviors, including chlordiazepoxide, alprazolam, and oxazepam.

Figure 2A:
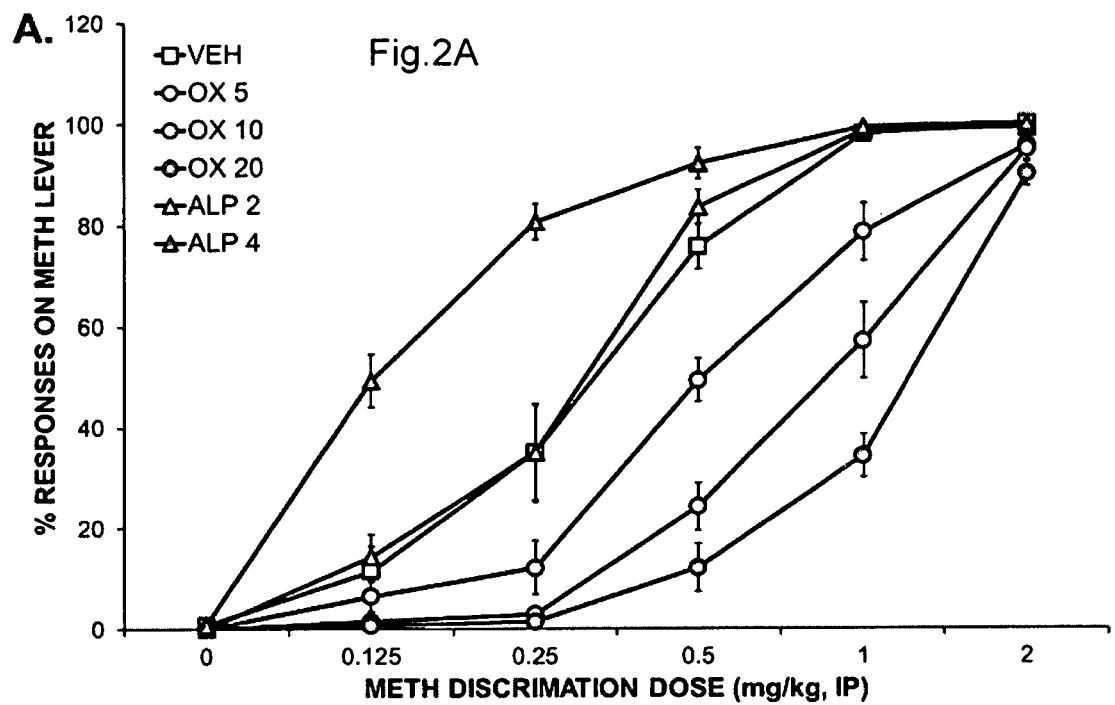
FIGS. 2A-2B are two graphs showing the effects of oxazepam (OX) and alprazolam (ALP) on drug discrimination, where alprazolam enhanced low-dose methamphetamine discrimination (FIG. 2A) but did not affect cocaine discrimination (FIG. 2B), and oxazepam decreased the discriminative stimulus effects of both MA and cocaine (FIGS. 2A and 2B)
Figure 2B:
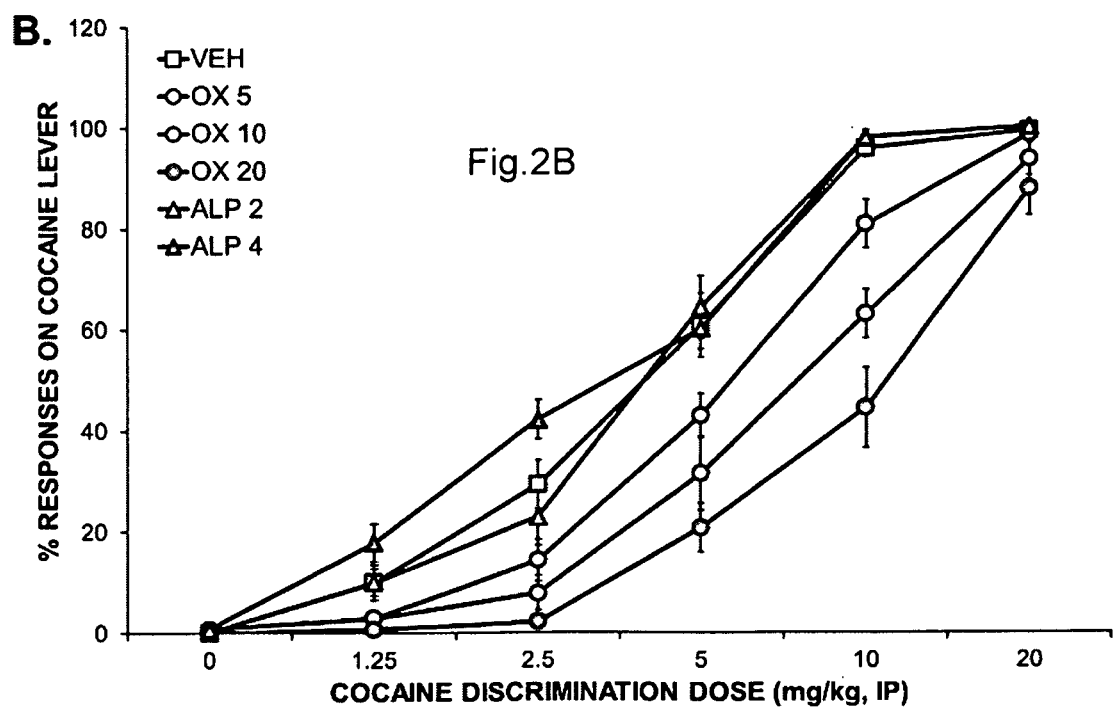
Figure 3:
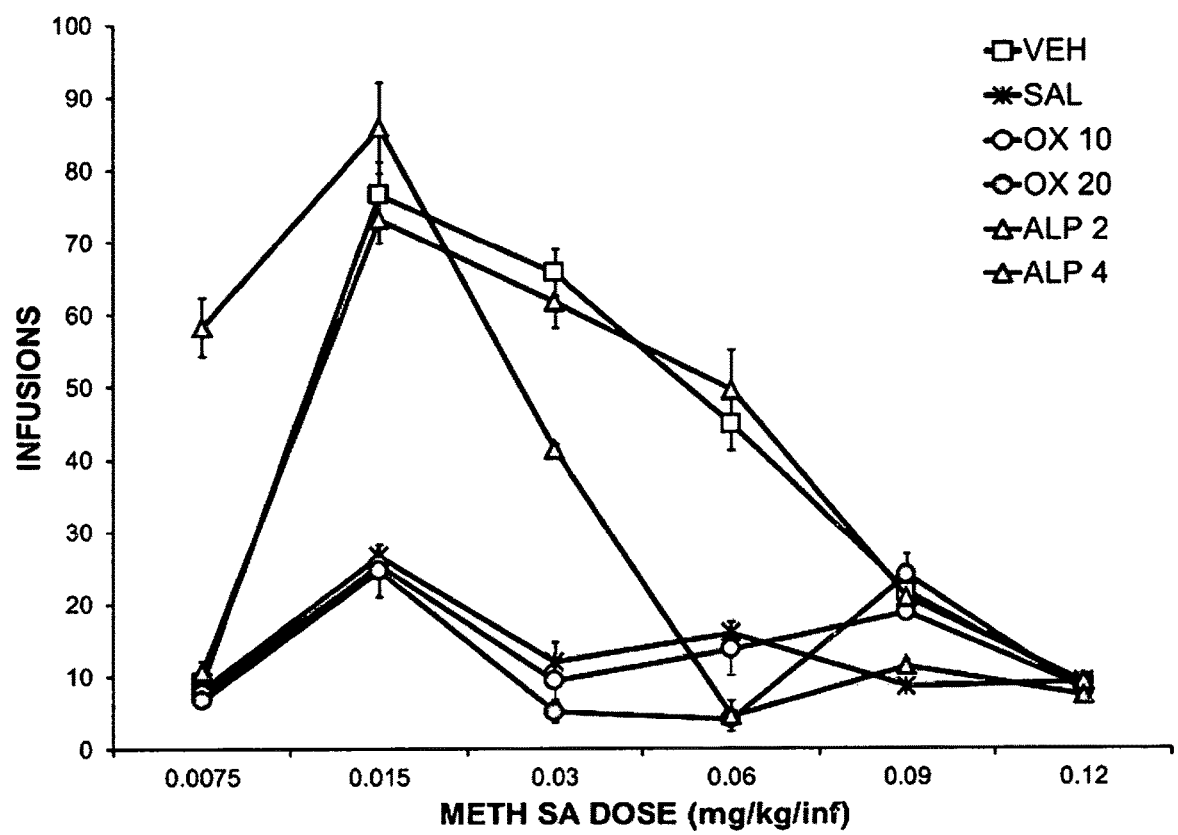
FIG. 3 is a graph that shows the effects of oxazepam and alprazolam on methamphetamine self-administration, where alprazolam (4 mg) enhanced low dose methamphetamine self-administration and oxazepam decreased methamphetamine self-administration responding at all doses tested.

However, evidence from the inventors' laboratory demonstrated that oxazepam and alprazolam differentially affect the discriminative stimulus effects of cocaine and methamphetamine in female rats. Adult female Wistar rats were trained to discriminate 1 mg/kg methamphetamine (IP) from saline using food pellet reinforcement according to previously published procedures (Mantsch and Goeders, 1999, 1998). Pretreatment with alprazolam (4 mg/kg, IP) enhanced the methamphetamine discriminative stimulus at doses of 0.125 and 0.25 mg/kg methamphetamine. As shown in FIGS. 2A and 2B, pretreatment with alprazolam had no effect on cocaine discrimination. However, pretreatment with oxazepam dose-dependently decreased the discriminative stimulus effects of both cocaine and methamphetamine. These results were supported by additional findings from the inventors' laboratory whereby oxazepam and alprazolam altered cocaine and methamphetamine self-administration in remarkably different ways. In male rats trained to self-administer methamphetamine (0.06 mg/kg/infusion), pretreatment with alprazolam (4 mg/kg, IP) resulted in significant increases in the self-administration of very low doses of the drug. On the other hand, as shown in FIG. 3, pretreatment with only oxazepam produced significant decreases in methamphetamine self-administration across all doses. These observations have been confirmed using a conditioned place preference model as well, evidencing that benzodiazepines differentially modulate the rewarding and reinforcing properties of methamphetamine. These data were further supported by a drug-induced reinstatement (D-IR) study. In the D-IR study, as shown in FIG. 4, oxazepam decreased methamphetamine-induced reinstatement while alprazolam actually potentiated the ability of a low-dose priming injection of methamphetamine to induce reinstatement. Thus, this is an extraordinarily consistent pattern across three very different models of drug-related behaviors. On the other hand, both oxazepam and alprazolam reduce cocaine-related behaviors in a similar manner.

The inventors conclude, based on such evidence, that the different effects between oxazepam and alprazolam stem from their differential binding to GABA$_A$ receptors and to the TSPO, and that these differences especially impact their actions on methamphetamine pharmacology.

Some effects of oxazepam and alprazolam on the subjective effects of d-amphetamine and methamphetamine have previously been reported, which at first blush appear to contradict the inventors finding. In contrast to the inventors' findings in rats, Rush and colleagues reported that alprazolam administration reduced some of the subjective effects of the methamphetamine "high" while oxazepam had no significant effect on the subjective effects of d-amphetamine (Lile et al., 2011, 2005). The differences between those results in humans and the inventors' data in rats are likely a result of the doses used as well as the differences in pharmacokinetics due to the route of administration. For example, significant differences are observed in the time to maximum methamphetamine concentrations in the blood ($T_{max}$) of humans when comparing intravenously administered methamphetamine (i.e., 6±11 min) to smoked (150±30 min), oral (216 min; range 180-300 min) or intranasal administration (169±8 min). In contrast, the $T_{max}$ for intraperitoneal methamphetamine injections in rats is 7.5±2.8 min, which is not significantly different from that measured following intravenous methamphetamine administration. Methamphetamine (or d-amphetamine) was administered intra-nasally or orally in the human studies, suggesting that $T_{max}$ would not have been reached in the Rush experiments as it was in the inventors' rat studies. In addition, in the Rush experiments the benzodiazepines were administered acutely at the same time as amphetamine, and oxazepam may not have had sufficient time to reach maximum blood levels as it is more slowly absorbed compared to alprazolam. Finally, the doses of d-amphetamine or methamphetamine tested in the human studies (i.e., up to 30 mg) were quite low. Intravenous methamphetamine users are known to inject doses as high as 250 mg at a time. Thus, the lack of reproducibility between the inventors' studies and those Rush conducted in humans are likely due to factors (e.g., dose, route of administration) that may be limited in the human laboratory due to ethical considerations, but such laboratory conditions may not be representative of the manner in which a typical human methamphetamine user actually uses methamphetamine.

The inventors are aware that oxazepam is one of the least desirable benzodiazepines by drug-dependent individuals. In contrast, alprazolam is consistently related as one of the most desired benzodiazepines by drug-dependent individuals. This difference between oxazepam and alprazolam is one of the reasons that the inventors have recently focused on oxazepam for its potential in treating drug-dependent subjects. The inventors conclude, based on the experimental evidence, that the differences in abuse liability between oxazepam and alprazolam stem from their differential interactions with $GABA_A$ receptors and the TSPO.

Figure 5A:
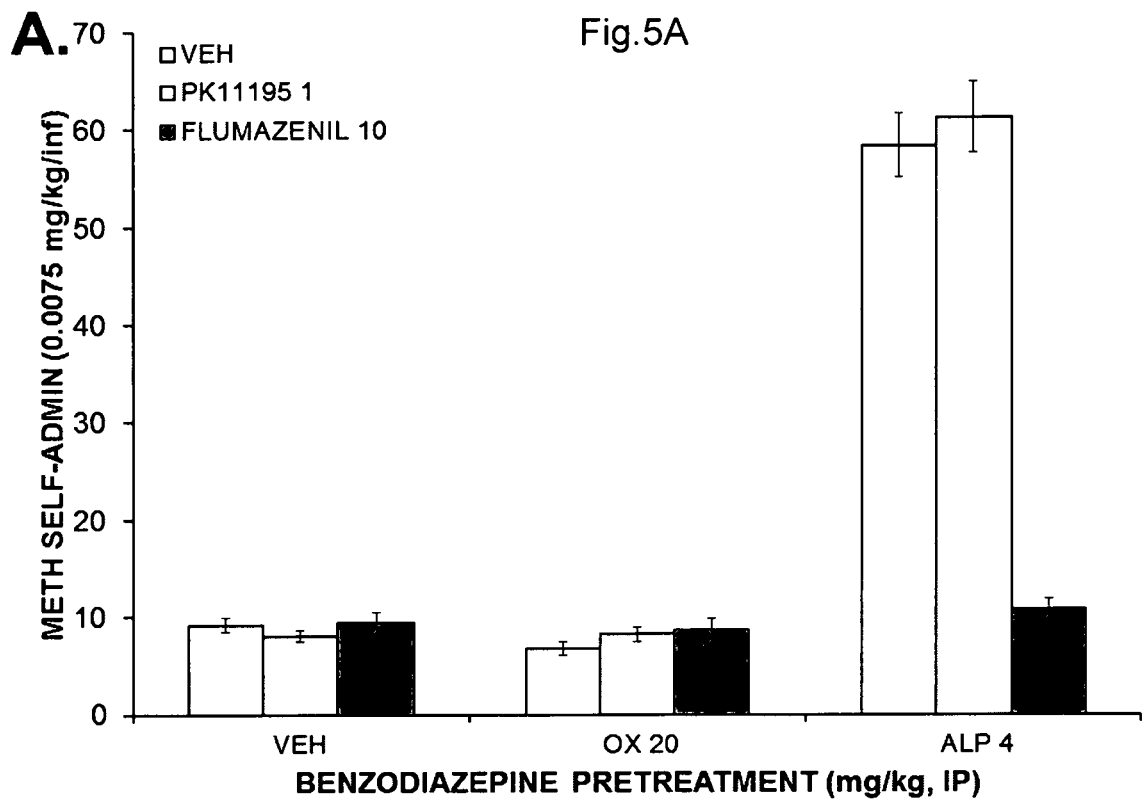
FIGS. 5A-5B are two bar graphs showing receptor dependence of oxazepam and alprazolam effects on methamphetamine self-administration, showing alprazolam enhanced low dose methamphetamine self-administration (FIG. 5A) and was blocked by flumazenil, and oxazepam decreased standard dose methamphetamine self-administration (FIG. 5B) and was partially blocked by PK11195 and flumazenil, and that oxazepam had no effect on low-dose methamphetamine self-administration (FIG. 5A)
Figure 5B:
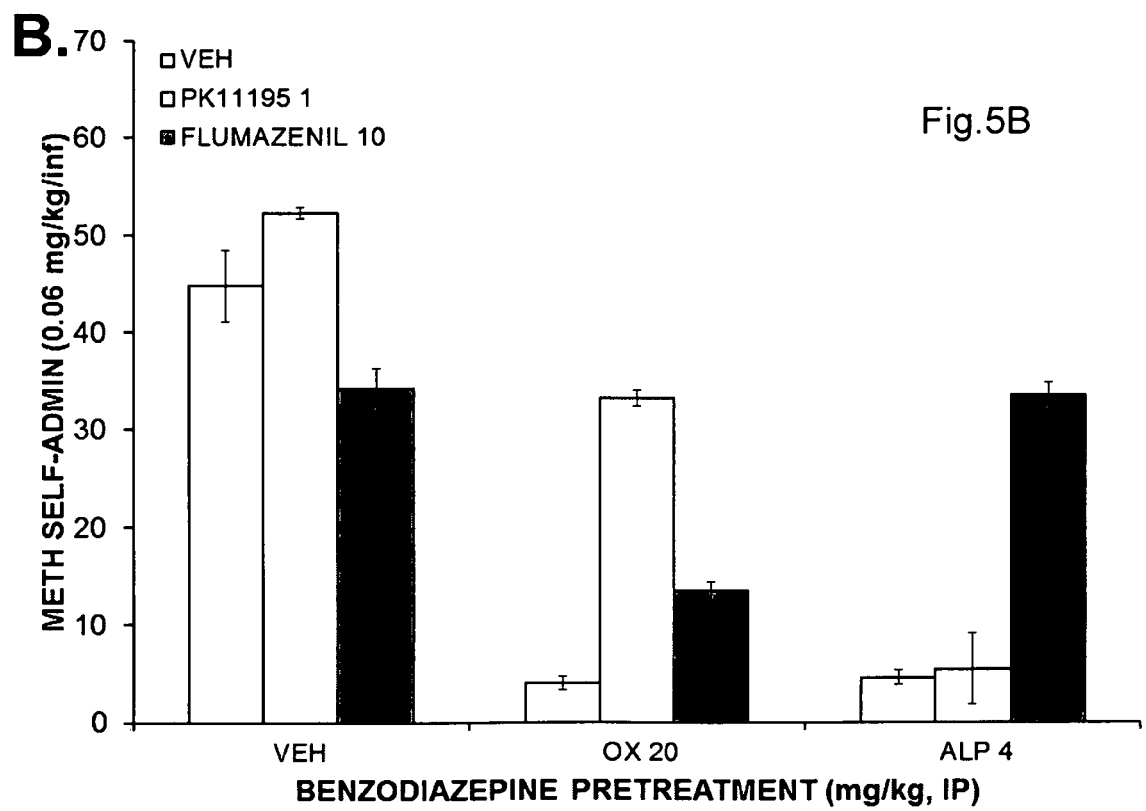

Such experiments include those to assess the receptors potentially responsible for the effects of oxazepam and alprazolam on methamphetamine self-administration in rats. When administered 30 minutes prior to alprazolam, the $GABA_A$ receptor antagonist flumazenil inhibited the effects of alprazolam on low-dose methamphetamine self-administration, suggesting a primary role of $GABA_A$ receptors. However, as shown in FIGS. 5A and 5B, oxazepam's effects on methamphetamine self-administration were also blocked by the TSPO antagonist, PKII195 in male rats, suggesting a central role for TSPO binding in the effects of oxazepam on methamphetamine-related behaviors.

Psychomotor stimulants and TSPO binding—The chronic administration of amphetamine derivatives results in significant microglial activation and proliferation. This injury can be monitored using imaging or binding techniques to analyze the up regulation of the TSPO. TSPO levels have been used as an indirect quantitative measure of microglial activation following chemically-induced brain insults, and the concomitant microglial activation has been employed as a marker of specific neurotoxic amphetamine-related damage. Subchronic, repeated doses of methamphetamine (4×10 mg/kg SC, every two hours) increase TSPO binding in the striatum, cerebellum and hippocampus within 72 hours. Self-administration of methamphetamine (0.3 mg/kg/inf) also enhances TSPO binding. Withdrawal from methamphetamine (1.0 mg/kg, IP, twice per day for 2 weeks, withdrawn for 7 days) also enhances TSPO mRNA in rats. This increase in TSPO is used as an indirect measure of neuroinflammation/microgliosis. A genetic knockout of IL-6, a major inflammatory factor, can attenuate the increased glial response to methamphetamine. Human methamphetamine users also display increases in TSPO binding measured using positron emission tomography (PET) imaging. This increased TSPO binding has also been correlated with the duration of methamphetamine use and abstinence. Methamphetamine has also been demonstrated to increase glial fibrillary acidic protein (GFAP) immunoreactivity, a well-established histopathological marker of glial activation and neuroinflammation.

TSPO, neurosteroids and neuroinflammation: TSPO agonists increase neurosteroid biosynthesis—One of the primary advantages to TSPO-favoring benzodiazepines is the downstream effects of TSPO activation. TSPO agonism induces changes in intracellular cholesterol trafficking such to promote the biosynthesis of several important steroid metabolites, including progesterone and allopregnanolone. These "neurosteroids" have fast actions on ion channels such as the $GABA_A$ receptor and are able to affect neuronal excitability in a paracrine manner. Neurosteroids such as allopregnanolone and tetrahydrodeoxycorticosterone (TH-DOC) are positive allosteric modulators at different $GABA_A$ receptor binding sites compared to benzodiazepines. TSPO agonism has been shown to be clinically relevant in anxiety and pain disorders, with no tolerance or withdrawal as seen with benzodiazepine treatment.

TSPO agonists and neurosteroids reduce neuroinflammation/neurodegeneration—TSPO ligands possess anti-inflammatory properties. This action may be mediated by modulation of mitochondrial function. Neurosteroids such as allopregnanolone and progesterone also possess neuroprotective and anti-inflammatory properties. The levels of these neurosteroids are altered by neurodegenerative processes and therefore, neurosteroids have become therapeutic candidates for many disorders. Allopregnanolone reduces traumatic brain injury-associated changes in inflammatory and apoptotic markers. Allopregnanolone also decreases neuronal loss in a number of neurodegenerative disorders including Parkinson's disease, Alzheimer's disease and amyotrophic lateral sclerosis. As discussed above, prolonged methamphetamine exposure enhances neuroinflammatory responses in rodent brains including enhanced GFAP expression and activated microglial phenotypes. This evidences that pharmacotherapies for methamphetamine abuse use should include compounds that affect neuroinflammation, including neurosteroids and TSPO ligands.

Neurosteroids reduce drug abuse and related deficits—Neurosteroids such as allopregnanolone may hold promise as pharmacological treatments for drug addiction as well. Allopregnanolone has been demonstrated to decrease methamphetamine-related responding in female rats as well as cocaine-related responding in both genders. Combining the anti-inflammatory properties and reward-decreasing properties of neurosteroids is another novel and innovative way to treat the cognitive and behavioral deficits associated with chronic methamphetamine abuse.

Thus, the inventors propose a novel approach for treating not only addiction to methamphetamine but also the medical (e.g., neuroinflarnrnation and cognitive deficits) and behavioral consequences of chronic methamphetamine exposure. Using benzodiazepine class compounds that modulate specific methamphetamine-induced behaviors and/or neuropathology are a novel pharmacotherapeutic treatment for methamphetamine. Targeting TSPO is an overlooked mechanism of action. Modulating a glial-based pharmacological target (i.e., the TSPO) is a novel treatment for neuropsychiatric disorders.

The inventors' research has demonstrated that certain specific benzodiazepine-related drugs can powerfully reduce methamphetamine-related behaviors in rats, a finding which the data evidences is related to benzodiazepine-induced TSPO activation. Other benzodiazepines may also activate TSPO and, therefore, based on such property would be useful in reducing methamphetamine-related behaviors. In further research, a further TSPO, Ro5-4864, was shown to also affect methamphetamine self-administration.

Structure-activity relationships evidence that benzodiazepines with a halogen moiety in the 4' position (i.e., bound to the 4' carbon—see generic benzodiazepine and affinity table above) possess higher affinity for TSPO and a much lower affinity for the $GABA_A$ receptor. Namely, compounds with the basic benzodiazepine structure, but with a halogen moiety (e.g., chlorine, fluorine, bromine, iodine) in the 4' position instead of the normal hydrogen. These compounds are referred to herein as TSPO compounds. Several drug compounds that meet such criteria are described in the table below.

Binding Affinity Table

Generic benzodiazepine

| Pos | TSPO | GABA |
|---|---|---|
| 1 | CH3 >> H | H = CH3 |
| 7 | Cl > F >> NO2 | Cl = NO2 > F |
| 4' | Cl > F > OCH3 >> NO2 | H > OH >> Cl > F |
| 2' | Cl > F > H | Cl > F > H |
| 3 | OH > H | H > OH |

Example TSPO Compounds

| Drug | Structural Position | | | | | | |
|---|---|---|---|---|---|---|---|
| | 1 | 7 | 4' | 2' | 3 | 6' | 4 |
| Ro5-5115 | CH3 | H | Cl | H | H | H | — |
| Ro5-5119 | CH3 | H | Cl | H | H | H | CH3 |
| Ro5-5120 | CH3 | NO2 | Cl | H | H | H | — |
| Ro5-5122 | CH3 | H | F | H | H | H | — |
| Ro5-5888 | CH3 | Cl | Cl | H | H | H | H |
| Ro5-4864 | CH3 | Cl | Cl | H | H | H | — |
| Ro5-6524 | CH3 | F | Cl | H | H | H | CH3 |
| Ro5-6528 | CH3 | F | Cl | H | H | H | H |
| Ro5-6531 | CH3 | F | Cl | H | H | H | — |
| Ro5-6900 | CH3 | Cl | Cl | Cl | H | H | — |
| Ro5-6902 | CH3 | Cl | Cl | H | H | H | H |
| Ro5-6945 | CH2CH=CH2 | Cl | Cl | H | H | H | — |
| Ro5-6993 | CH2CH3 | Cl | Cl | H | H | H | — |
| Ro7-9277 | CH3 | Cl | Cl | H | OH | H | — |

The structural names (and Chemical Abstracts Service Registry numbers or "CAS #" where available) for the above compounds and other benzodiazepine ligands shown in FIGS. 1A-1D are listed in the table below:

| Compound | Structure | CAS # |
|---|---|---|
| Ro5-5115 | 4'-chloro-1,3-dihydro-1-methyl-5-phenyl-2H-1,4-benzodiazepin-2-one | N/A |
| Ro5-5119 | 4'-chloro-1,3-dihydro-1,4-dimethyl-5-phenyl-2H-1,4-benzodiazepin-2-one | N/A |
| Ro5-5120 | 4'-chloro-1,3-dihydro-1-methyl-7-nitro-5-phenyl-2H-1,4-benzodiazepin-2-one | N/A |
| Ro5-5122 | 4'-Fluoro-1,3-dihydro-1-methyl-5-phenyl-2H-1,4-benzodiazepin-2-one | N/A |
| Ro5-5888 | 4',7-Dichloro-1,3,4-trihydro-1-methyl-5-phenyl-2H-1,4-benzodiazepin-2-one | N/A |
| Ro5-4864 | 4',7-Dichloro-1,3-dihydro-1-methyl-5-phenyl-2H-1,4-benzodiazepin-2-one | N/A |
| Ro5-6524 | 4'-Chloro-7-fluoro-1,3-dihydro-1,4-dimethyl-5-phenyl-2H-1,4-benzodiazepin-2-one | N/A |
| Ro5-6528 | 4'-Chloro-7-fluoro-1,3,4-trihydro-1,4-dimethyl-5-phenyl-2H-1,4-benzodiazepin-2-one | N/A |
| Ro5-6531 | 4'-Chloro-7-fluoro-1,3-dihydro-1-methyl-5-pheny1-2H-1,4-benzodiazepin-2-one | N/A |
| Ro5-6900 | 2',4',7-trichloro-1,3-dihydro-1-methyl-5-phenyl-2H-1,4-benzodiazepin-2-one | N/A |
| Ro5-6902 | 4',6',7-Trichloro-1,3,4-trihydro-1-methyl-5-phenyl-2H-1,4-benzodiazepin-2-one | N/A |
| Ro5-6945 | 1-allyl-4',7-dichloro-1,3-dihydro-5-phenyl-2H-1,4-benzodiazepin-2-one | N/A |
| Ro5-6993 | 4',7-dichloro-1-ethyl-1'3-dihydro-5-phenyl-2H-1,4-benzodiazepin-2-one | N/A |
| Ro7-9277 | 4',7-dichloro-1-hydro-3-hydroxy-1-methyl-5-phenyl-2H-1,4-benzodiazepin-2-one | N/A |
| Diazepam | 7-chloro-1,3-dihydro-1-methyl-5-phenyl-2H-1,4-benzodiazepin-2-one | 439-14-5 |
| Oxazepam | 7-chloro-1,3-dihydro-3-hydroxy-5-phenyl-2H-1,4-benzodiazepin-2-one | 604-75-1 |
| Alprazolam | 8-chloro-1-methyl-5-phenyl-4H-(1,2,4)triazolo-1,4-benzodiazepine | 28981-97-7 |

Figure 6:
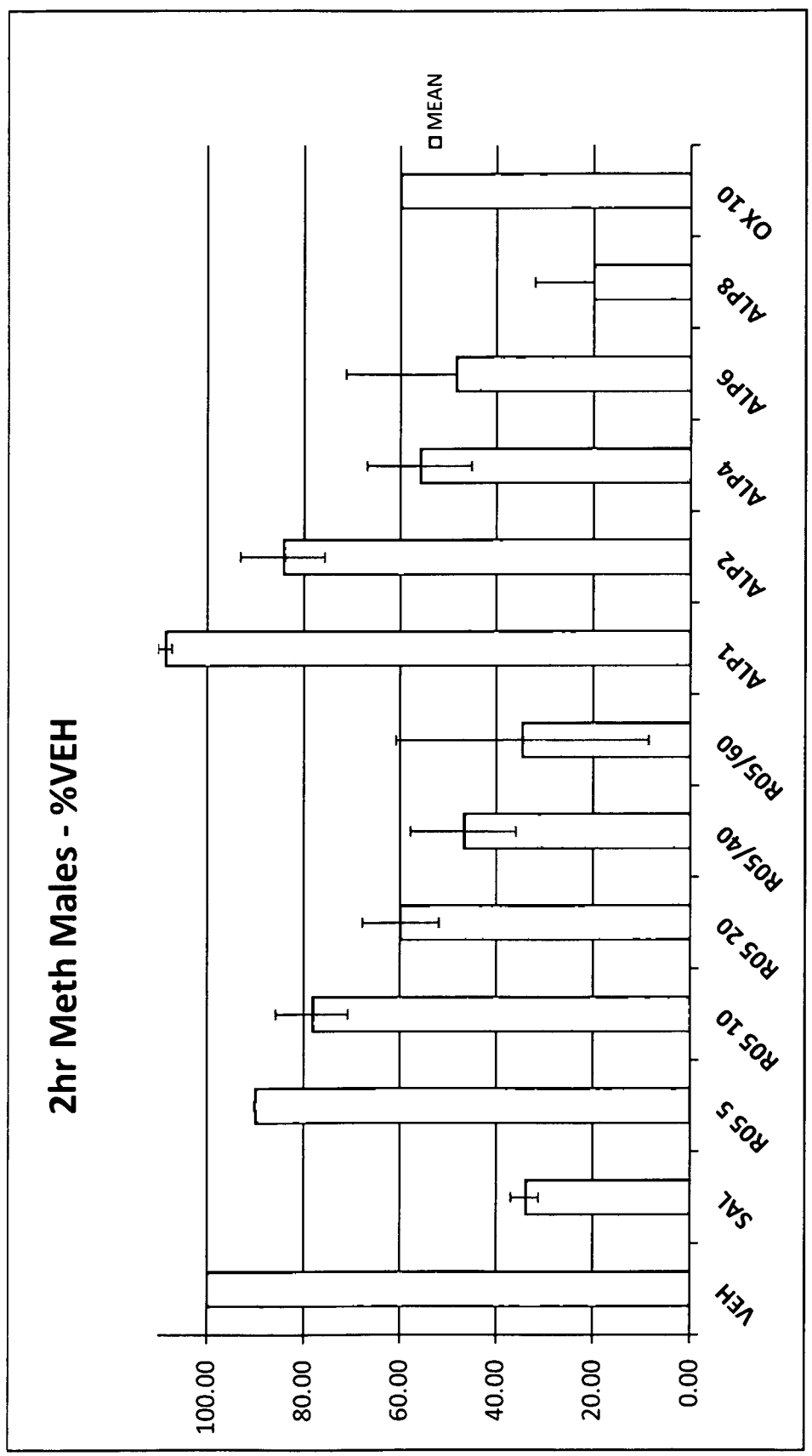
FIG. 6 is bar graph showing the effects of Ro5-4864, oxazepam and alprazolam on methamphetamine self-administration with male rats.
Figure 7:
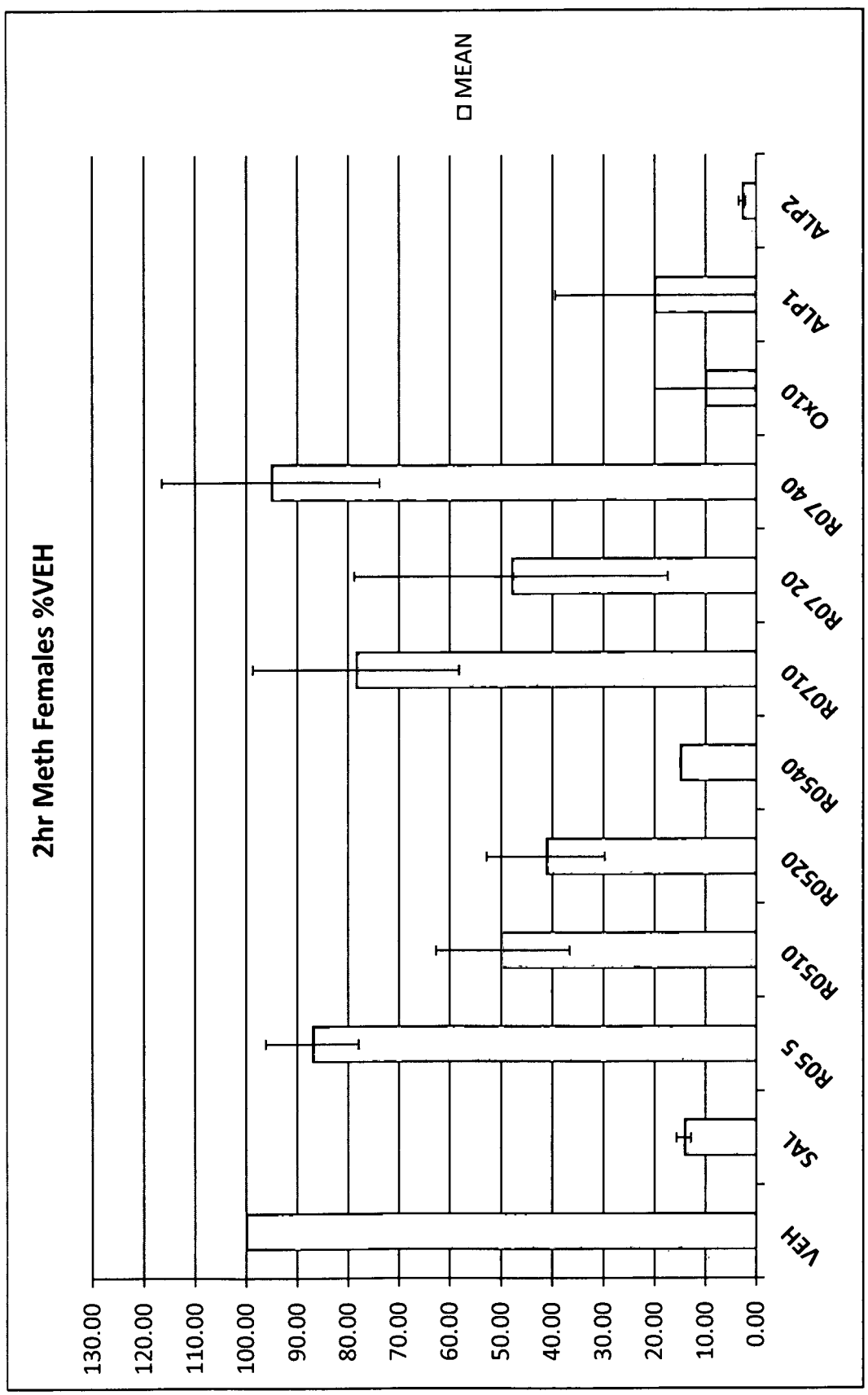
FIG. 7 is bar graph showing the effects of Ro5-4864, Ro7-9277, oxazepam and alprazolam on methamphetamine self-administration with female rats, showing females of the species appear to be significantly more sensitive to the effects of Ro5-4864 compared to the males of the species.

Turning to FIGS. 6 and 7, the inventors tested the TSPO compound Ro5-4864 in an animal model of methamphetamine self-administration in male and female rats. The experiments demonstrated a dose-related decrease in methamphetamine self-administration confirming a role for TSPO in methamphetamine reward. These data suggest that the TSPO may be a viable target for methamphetamine dependence. The inventors compared these effects to the effects of the benzodiazepine alprazolam. Ro5-4864 may be superior to alprazolam due to the abuse potential of alprazolam. As shown in FIG. 7 female rats appear to be significantly more sensitive to the effects of Ro5-4864 compared to male rats. The inventors also show preliminary data with Ro7-9277 with female rats.

Based on the experimental results, the inventors propose the use of the TSPO compounds to decrease methamphetamine-seeking and methamphetamine-taking behaviors by decreasing the activation of brain circuits involved in methamphetamine craving. The inventors also propose the use of the TSPO compounds to reduce other cognitive and behavioral effects of methamphetamine. Methamphetamine users often exhibit neurocognitive impairments and are more likely to engage in risky sexual behaviors that promote sexual-transmitted infections such as HIV. Chronic methamphetamine use and HIV infection both induce a neuroinflammatory response characterized by a marked increase in TSPO binding and microglial activation. TSPO activation decreases sexual behavior and enhances memory functions, especially in animal models of neuroinflammation or neurodegeneration. Therefore, targeting TSPO activation as part of such treatment will decrease the neuroinflammatory response and alleviate the neurocognitive effects associated with prolonged methamphetamine use. While the treatment is evidenced to be effective for both males and females, one target patient group is methamphetamine addicted females. The higher sensitivity of females to Ro5-4864 further underscores females as a target patent group for this treatment.

The inventors propose treatment of methamphetamine users and HIV infected individuals with the TSPO compounds. Ro5-4864 is a prototype TSPO compound which was shown to have does responsive effects. Based on experimental evidence the inventors concluded that TSPO compounds reduce craving (or seeking) for methamphetamine, substantially halt and can at least partially reverse the cognitive deficits produced by methamphetamine use, and reduce the incidence of increased risky sexual behaviors induced by methamphetamine. By reducing the occurrence of methamphetamine-induced sexual behaviors, and by decreasing the neuroinflammatory response associated with HIV, TSPO compounds could be one strategy used to reduce the consequences of HIV/AIDS in methamphetamine users.

The invention includes pharmaceutical compositions comprising a TSPO compound acting as a peripheral benzodiazepine receptor ligand in combination with one or more compatible pharmaceutically acceptable adjuvants or diluents which may be inert or physiologically active. These compositions may be administered by the oral, parenteral or rectal route or locally. The TSPO compound acting as a peripheral benzodiazepine receptor ligand may be may be selected from the group including Ro5-5115, Ro5-5119, Ro5-5120, Ro5-5122, Ro5-5888, Ro5-4864, Ro5-6524, Ro5-6528, Ro5-6531, Ro5-6900, Ro5-6902, Ro5-6945, Ro5-6993, Ro7-9277, and oxazepam, for example, and therapeutically acceptable salts, solvates, clathrates, stereoisomers, enantiomers or prodrugs of these compounds or mixtures thereof.

Other classes of drugs which would potentiate the actions of TSPO compounds when used in combination with the TSPO compounds are agonists (activators) of potassium-chloride co-transporter 2 (KCC2) and inhibitors (antagonists) of 20 alpha-hydroxysteroid dehydrogenase (20 alpha-HSD). A combination of TSPO with one or more agonists of KCC2 and one or more inhibitors of 20 alpha-HSD may also be used.

Agonists (activators) of potassium-chloride co-transporter 2 (KCC2)—

These compounds activate the chloride extrusion pump in neurons (KCC2) to modify the driving force for chloride ions across the neuronal membrane. The inventors have observed that KCC2 agonists enhance the activity of other GABAergic drugs, including neurosteroids and benzodiazepines. Therefore, it follows that the combination of KCC2 agonist and TSPO compound would enhance therapeutic effects by increasing the efficacy of downstream signaling events including GABA-gated chloride influx. Specific KCC2 activators could include CLP257 [(5Z)-5-[(4-Fluoro-2-hydroxyphenyl)methylene]-2-(tetrahydro-1-(2H)-pyridazinyl)-4(5H)-thiazolone].

Inhibitors (antagonists) of 20 alpha-hydroxysteroid dehydrogenase (20 alpha-HSD)—This enzyme is responsible for the catabolism of GABA-active active neurosteroids. It follows that a combination of 20 alpha-HSD inhibitor and TSPO compound would further enhance the levels of therapeutic neurosteroids by both enhancing the early steps of neurosteroid biosynthesis and preventing enzymatic breakdown by 20 alpha-HSD. Specific 20 alpha-HSD inhibitors could include STZ26 (D-homo-16-oxa-4-androstene-3,16alpha-dione), 3-chloro-5-phenylsalicylic acid and 3-bromo-5-phenylsalicylic acid.

Tablets, pills, powders (gelatin capsules or cachets) or granules may be used as solid compositions for oral administration. In these compositions, the active ingredient according to the invention may be mixed with one or more inert diluents such as starch, cellulose, sucrose, lactose or silica. These compositions may also contain substances other than diluents, for example one or more lubricants such as magnesium stearate or talcum, a colorant, a coating (dragees) or a lacquer.

Pharmaceutically acceptable solutions, suspensions, emulsions, syrups and elixirs containing inert diluents such as water, ethanol, glycerol, benzoic acid, benzyl alcohol, sodium benzoate, dimethyl sulfoxide, vegetable oils or liquid paraffin may be used as liquid compositions for oral administration. These compositions may contain substances other than diluents, for example wetting agents, sweeteners, thickeners, flavoring agents or stabilizers.

Sterile compositions for parenteral administration may preferably be non-aqueous solutions, suspensions or emulsions. Water, propylene glycol, polyethylene glycol, benzoic acid, benzyl alcohol, sodium benzoate, dimethyl sulfoxide, vegetable oils, especially olive oil, injectable organic acids esters, for example ethyl oleate or other suitable organic solvents may be used as the solvent or the carrier.

These compositions may also contain adjuvants, especially wetting agents, tonicity regulating agents, emulsifiers, dispersants and stabilizers. The sterilization may be carried out in several ways, for example by aseptic filtration, incorporating a sterilizing agent, by irradiation or by heating. They may also be prepared in the form of sterile solid compositions which may be dissolved at the time of use in a sterile medium suitable for injection.

Compositions for rectal administration are suppositories or rectal capsules, which contain, in addition to the active product, excipients such as cocoa butter, semi-synthetic glycerides or polyethylene glycols.

Compositions for local administration may be for example creams, ointments, lotions, eye lotions, mouth-washes, nasal drops or aerosols.

The dosage depends on the effect sought, the length of treatment and the administration route employed. In general, the medical practitioner will determine the appropriate dosage depending on the age, weight and all other factors specific to the subject to be treated. The compositions would preferably be administered similar to other clinically-relevant benzodiazepines (rats: 1-50 mg/kg, intraperitoneally; humans: 0.01-20.0 mg/kg, with the most preferable range being 1-10 mg/kg body weight per day orally).

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, we claim:

1. A method of treating a condition in a human patient comprising:
   pharmacologically activating a translocator protein of 18 kDa (TSPO) by administering a therapeutically effective amount of a pharmaceutical composition to the patient;
   wherein the pharmaceutical composition includes one or more peripheral benzodiazepine receptor ligands, or one or more therapeutically acceptable salts, clathrates, stereoisomers, or enantiomers, of these compounds or mixtures thereof, which activate the TSPO;
   wherein the condition is one of
   a chronic methamphetamine addiction;
   a medical consequence of methamphetamine use; and
   a behavioral consequence of methamphetamine use.

2. The method of claim 1 wherein the condition is chronic methamphetamine addiction.

3. The method of claim 1 wherein the condition is a medical consequence of methamphetamine use.

4. The method of claim 3 wherein the medical consequence is cognitive defect.

5. The method of claim 1 wherein the condition is a behavioral consequence of methamphetamine use.

6. The method of claim 5 wherein the behavioral consequence is one of increased violence, risk-taking behaviors, propensity for criminal activity, and aberrant sexual behavior.

7. The method of claim 1 wherein the human is a female.

8. The method of claim 1 wherein the pharmaceutical composition includes a benzodiazepine that targets TSPO over a GABAA receptor.

9. The method of claim 8 further comprising administering a therapeutically effective amount of one or more of an agonist (activator) of potassium-chloride co-transporter 2 (KCC2) and an inhibitor (antagonist) of 20alpha-hydroxysteroid dehydrogenase (20alpha-HSD) and therapeutically acceptable salt, clathrate, stereoisomer or enantiomer of these compounds or mixtures thereof.

10. The method of claim 1 wherein the pharmaceutical composition includes a benzodiazepine that has a halogen bound to a 4' carbon in the benzodiazepine.

11. The method of claim 1 wherein the pharmaceutical composition includes one or more peripheral benzodiazepine receptor ligands selected from a group consisting of: Ro5-5115, Ro5-5119, Ro5-5120, Ro5-5122, Ro5-5888, Ro5-4864, Ro5-6524, Ro5-6528, Ro5-6531, Ro5-6900, Ro5-6902, Ro5-6945, and Ro5-6993, oxazepam and therapeutically acceptable salt, clathrate, stereo isomer or enantiomer of these compounds or mixtures thereof.

12. The method of claim 11 wherein the peripheral benzodiazepine receptor ligands is one of Ro5-4864, oxazepam and therapeutically acceptable salt, clathrate, stereo isomer or enantiomer of these compounds or mixtures thereof.

* * * * *